(12) United States Patent
Densford et al.

(10) Patent No.: US 8,057,523 B2
(45) Date of Patent: Nov. 15, 2011

(54) SET SCREW WITH DEFORMABLE MEMBER

(75) Inventors: Eric Daniel Densford, Memphis, TN (US); Jim Michael Mirda, Memphis, TN (US); Christopher M. Patterson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 719 days.

(21) Appl. No.: 12/178,412

(22) Filed: Jul. 23, 2008

(65) Prior Publication Data

US 2010/0023063 A1 Jan. 28, 2010

(51) Int. Cl.
*A61B 17/86* (2006.01)

(52) U.S. Cl. ......................................... 606/308; 606/270

(58) Field of Classification Search .................. 606/270, 606/308; 411/156, 393
See application file for complete search history.

(56) References Cited

U.S. PATENT DOCUMENTS

| | | | |
|---|---|---|---|
| 936,549 A * | 10/1909 | Lundholm | 411/393 |
| 1,107,077 A | 8/1914 | Kenworth | |
| 3,479,072 A | 11/1969 | Kosar | |
| 3,501,993 A | 3/1970 | Swenson | |
| 3,645,161 A | 2/1972 | Wesker | |
| 4,671,716 A | 6/1987 | Grass | |
| 6,116,832 A | 9/2000 | Wolf et al. | |
| 6,960,212 B2 | 11/2005 | Richelsoph et al. | |
| 7,320,570 B2 | 1/2008 | Czarnek | |
| 7,516,991 B1 * | 4/2009 | Cheng | 285/404 |
| 2003/0185648 A1 | 10/2003 | Blaess | |
| 2005/0180839 A1 | 8/2005 | Czarnek | |

* cited by examiner

*Primary Examiner* — Nicholas Woodall

(57) ABSTRACT

The present application is directed to set screws used with fasteners to capture and engage an elongated member. The set screws include a body sized to attach to a receiver of the fastener. A deformable member may be attached to an end of the set screw and provides for the set screw to more fully engage the elongated member to prevent potential damage to the elongated member and prevent the set screw from backing out of the fastener. In one embodiment, just the deformable member contacts the elongated member. In another embodiment, the deformable member and the body contact the elongated member. In yet another embodiment, a contact member is attached to the deformable member to contact against the elongated member.

5 Claims, 5 Drawing Sheets

SET SCREW WITH DEFORMABLE MEMBER

BACKGROUND

The present application is directed to set screws used for use with fasteners to attach an elongated member to a bone and, more particularly, to set screws with a deformable member that increases the contact with the elongated member to prevent back-out of the set screw from the fastener and/or damage to the elongated member.

Set screws are often used with fasteners to attach an elongated member to a bone within a patient. Examples of fasteners include but are not limited to multi-axial screws, fixed-angle screws, and offset screw connectors. The fasteners may include a receiver with a receptacle to receive the elongated member, and an anchor (e.g., screw, hook) that attaches to the bone. The fasteners may be constructed as a single piece, or may include multiple pieces that are attached together such as a multi-axial screw that includes a receiver body that attaches to a head of bone screw. The elongated member fits within the receptacle of the receiver, and the set screw attaches to the receiver to prevent escape of the elongated member. The set screw may also apply a force to the elongated member to maintain the attachment within the receiver. The fasteners may be configured to receive a variety of different elongated members, including but not limited to rods, cables, and wires.

Often times the receiver is configured to allow the elongated member to be positioned at a variety of angles within the receptacle. This is problematic as the set screw does not fully contact against the elongated member. This may lead to the loosening of the set screw from the receiver and/or backing out of the set screw from the receiver. Additionally, this incomplete contact may damage the elongated member and causing notching or deformation.

SUMMARY

The present application is directed to set screws used with fasteners to capture and engage an elongated member. The set screws include a body sized to attach to a receiver of the fastener. A deformable member may be attached to an end of the set screw and provides for the set screw to more fully engage the elongated member and secure it within the receiver. The deformable member may also prevent potential damage to the elongated member and prevent the set screw from backing out of the fastener. In one embodiment, just the deformable member contacts the elongated member. In another embodiment, the deformable member and the body contact the elongated member. In yet another embodiment, a contact member is attached to the deformable member to contact against the elongated member.

The various aspects of the various embodiments may be used alone or in any combination, as is desired.

DETAILED DESCRIPTION

Figure 1:
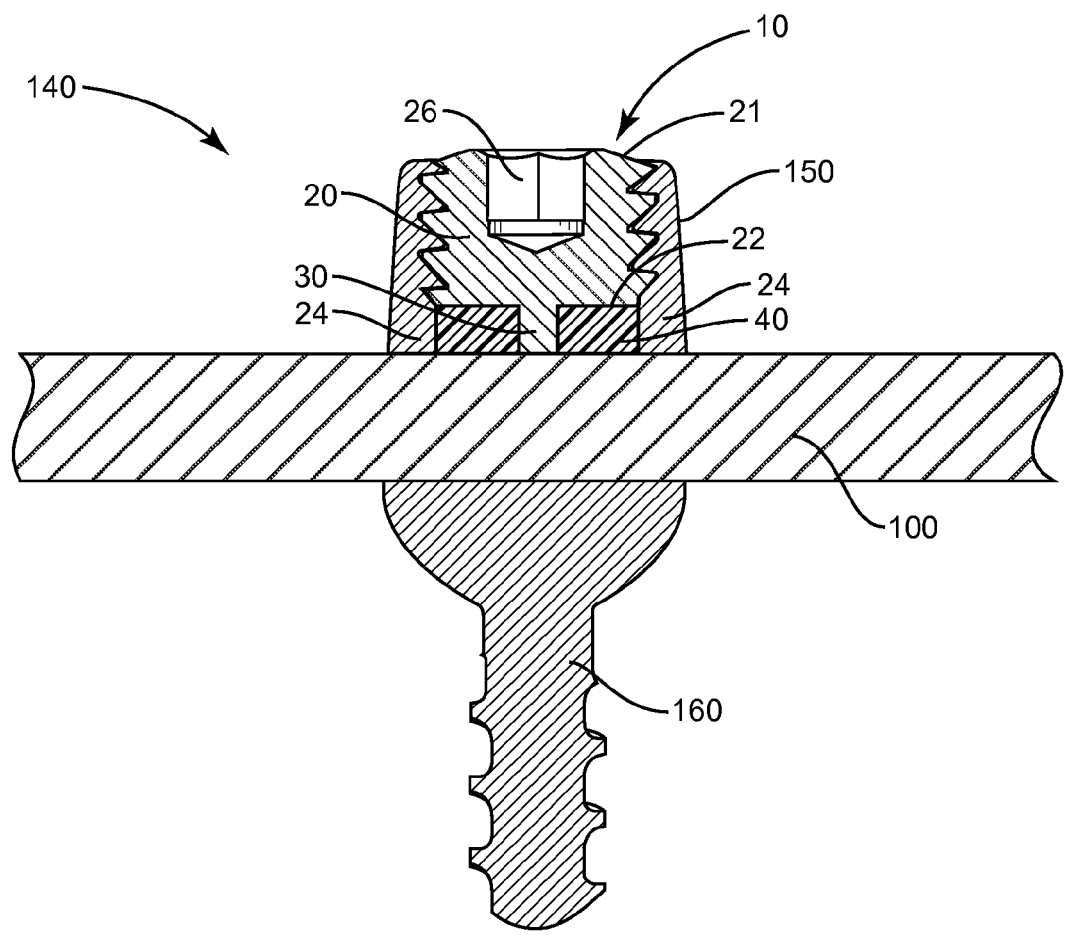
FIG. 1 is a schematic sectional view of a set screw with a deformable member according to one embodiment.

The present application is directed to set screws for use with fasteners for attaching an elongated member to a bone within a patient. The set screws engage with the elongated member to capture and secure the elongated member within a receptacle of the fastener. FIG. 1 includes one embodiment of a set screw 10 that engages with a receiver 150 of a fastener 140. The set screw 10 includes a body 20 that engages with the receiver 150. A member 40 is attached to the body 20 to facilitate engagement of the set screw 10 with the elongated member 100. The member 40 is constructed from a super elastic material that deforms to the shape of the elongated member 100 when the body 20 is engaged with the receiver 150. In this embodiment, the member 40 directly contacts against the elongated member 100.

Figure 2:
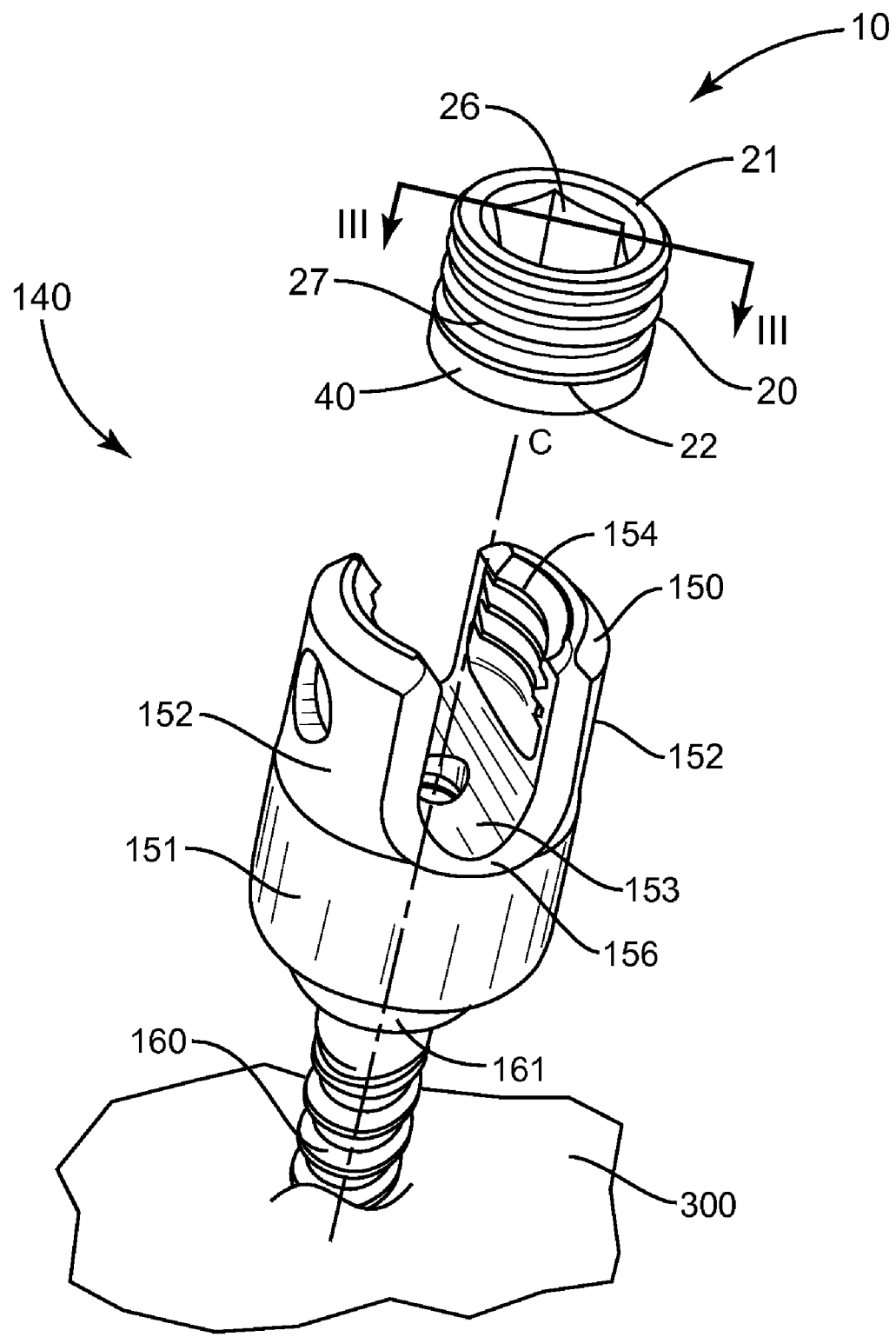
FIG. 2 is an exploded perspective view of a set screw according to one embodiment.

The set screw 10 may be used in various types of fasteners 140. FIG. 2 includes one embodiment of fastener 140 that includes the set screw 10, a receiver 150, and an anchor 160. A head 161 of the anchor 160 is pivotally coupled to a base 151 of the receiver 150. The anchor 160 may include threads for insertion into a bone 300, and in one embodiment the anchor 160 is a pedicle screw. The receiver 150 includes the base 151 and opposed uprights 152 forming a U-shaped channel 153 within which the elongated member 100 (not illustrated in FIG. 2). The uprights 152 may include threads 154 to engage with threads 27 on the set screw 10.

The fastener 140 of FIG. 2 provides for the receiver 150 to pivot relative to the anchor 160 to accommodate the elongated member 100 at a variety of different angular positions. Uprights 152 may also include chamfered edges 156 to also allow for the elongated member 100 to be positioned at various angles. FIG. 2 illustrates a centerline C of the receiver 150 substantially aligned with a centerline of the anchor 160. The receiver 150 may be pivoted relative to the anchor 160 such that the centerline C is positioned at various angles relative to a centerline of the anchor 160.

Figure 5:
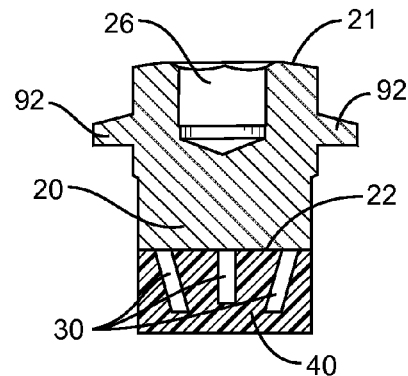
FIG. 5 is a schematic sectional view of a set screw with a deformable member according to one embodiment.

The set screw 10 attaches to the receiver 150 to capture and secure the elongated member 100 within the channel 153. The set screw 10 includes a body 20 sized to fit between and engage the uprights 152. In the embodiment of FIG. 2, body 20 includes a substantially cylindrical shape with a first end 21 and a second end 22. The length measured between the ends 21, 22 and the width measured between the lateral sides of the body 20 may vary depending upon the size of the receiver 150. First end 21 may include a receiver 26 to engage with a tool to rotating the body 20 into and out of the receiver 150. The exterior of the body 20 may include threads 27 that mate with the corresponding threads 154 on the receiver 150. The threads 27 may extend the entire length of the body 20, or a lesser amount. In another embodiment as illustrated in FIG. 5, the body 20 is not threaded but rather includes one or more outwardly-extending tabs 92 that fit within slots in the uprights 152. The slots include cam surfaces that engage with the tabs 92 during rotation of the body 20 to engage the body 20 with the receiver 150.

Figure 3:
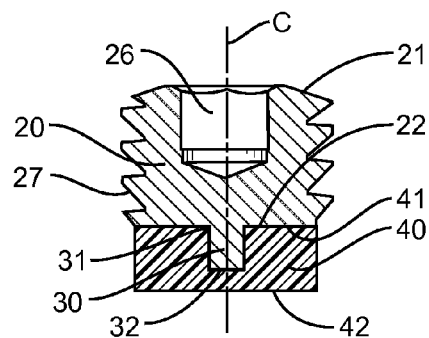
FIG. 3 is a sectional view cut along line III-III of FIG. 2 of a set screw with a deformable member according to one embodiment.
Figure 4:
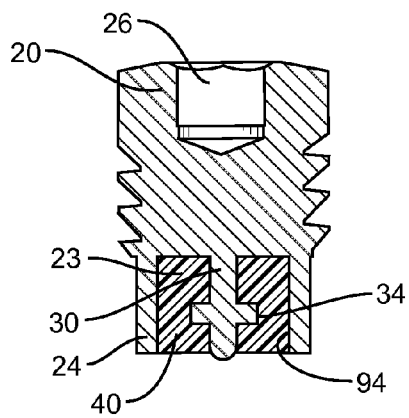
FIG. 4 is a schematic sectional view of a set screw with a deformable member according to one embodiment.

Various elements may extend outward from the second end 22 to facilitate attachment with the member 40 and/or contact with the elongated member 100. These elements may be attached with the body 20, or may be formed with the body 20 (i.e., the body and element(s) are of a one-piece unitary construction). FIG. 3 includes an extension 30 that extends outward from the second end 22. Extension 30 includes a base 31 at the second end 22 of the body 20 and a tip 32 positioned away from the body 20. The extension 30 may be straight and coaxial with the centerline C of the body 20. FIG. 4 illustrates that the extension 30 may also include one or more outwardly-extending branches 34 positioned between the base 31 and tip 32. Branches 34 strengthen the attachment of the member 40. FIG. 5 includes an embodiment with multiple extensions 30 that extend outward from various locations along the second end 22 of the body 20. Further, extensions 30 in the various embodiments may extend outward from the second end 22 at various angles.

Figure 6:
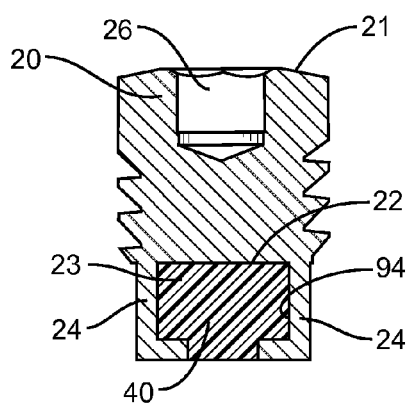
FIG. 6 is a schematic sectional view of a set screw with a deformable member according to one embodiment.

A sidewall 24 may also extend outward from the second end 22 of the body 20. As illustrated in FIGS. 4 and 6, the sidewall 24 may extend around the periphery of the second end 22 and forms a recess 23 that receives the member 40. The length of the sidewall 24 and corresponding depth of the recess 23 may vary depending upon the specific embodiment of the member 40. An inner surface 94 of the sidewall 24 may be parallel to the centerline C of the body 20, or may be at a transverse angle to the centerline C.

Body 20 may be constructed from various elements, including but not limited to titanium, cobalt-chrome, and stainless steels.

The member 40 is attached to the second end 22 to facilitate the engagement between the set screw 10 and the elongated member 100. Member 40 is made from a superelastic material that allows for deformation around the elongated member 100. This deformation allows the set screw 10 to more fully capture the elongated member 100 and prevent the set screw 10 from backing out of the receiver 150. The deformation and more complete contact may also protect the elongated member 100 against notching and deformation. In one embodiment, member 40 is made from polyetheretherketone (PEEK). Member 40 may also be made from other materials including but not limited to polyetherketone (PEK), polyaryletherketone (PAEK), silicone, BIONATE thermoplastic polycarbonate urethane, styrene-butadiene, polyisoprene, and combinations thereof. Member 40 may be attached to the body 20 in a variety of different manners including but not limited to molding, snap fit, and adhesives. In one embodiment, the member 40 is attached to prevent rotation relative to the body 20.

Figure 7:
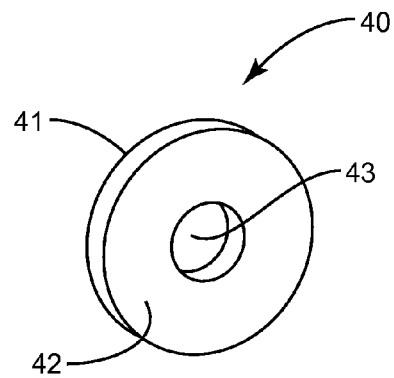
FIG. 7 is a perspective view of a member according to one embodiment.
Figure 8:
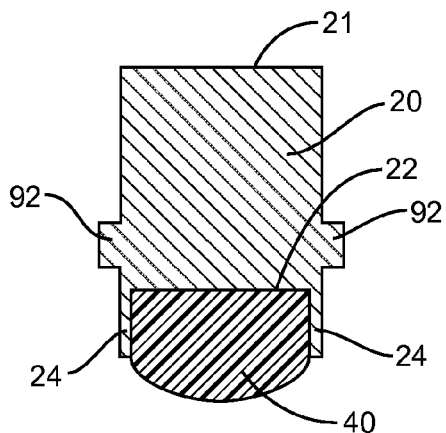
FIG. 8 is a schematic sectional view of a set screw with a deformable member according to one embodiment.

Member 40 may include various shapes and sizes. Member 40 includes a first side 41 that faces towards the body 20 and a second side 42 that faces away from the body 20. An aperture 43 may extend through the member 40 and be positioned to receive the extension 30. The size of the aperture may closely approximate the size of the extension 30, or may be substantially larger than the extension 30 thus forming a gap between the member 40 and extension 25. A thickness of the member 40 measured between the first and second sides 41, 42 may be substantially the same throughout as illustrated in FIG. 7, or may vary as illustrated in FIG. 8. Further, member 40 may be flat or curved.

In one embodiment, member 40 is attached to the body 20 such that only the member 40 contacts the elongated member 100. FIG. 3 includes one embodiment with the second side 42 of the member 40 extending outward beyond the second end 22 and extension 30. When the set screw 10 is engaged with the receiver 150, the member 40 contacts the elongated member 100 and spaces the body 20 apart. FIG. 8 includes another embodiment with the member 40 extending outward beyond the sidewall 24 such that it alone contacts the elongated member 100.

In another embodiment, a combination of the member 40 and extensions 30 and/or sidewall 24 contact the elongated member 100. FIG. 1 includes one embodiment with the extension 30, sidewall 24, and member 40 each contacting the elongated member 100. In one embodiment, one or both of the extension 30 and sidewall 24 includes a narrowed tip to limit an amount of contact with the elongated member 100.

Figure 9:
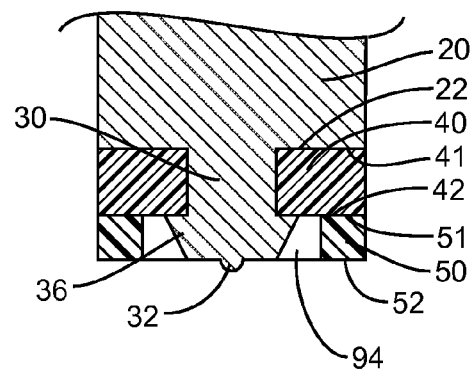
FIG. 9 is a partial schematic sectional view of a set screw with a deformable member according to one embodiment.
Figure 10:
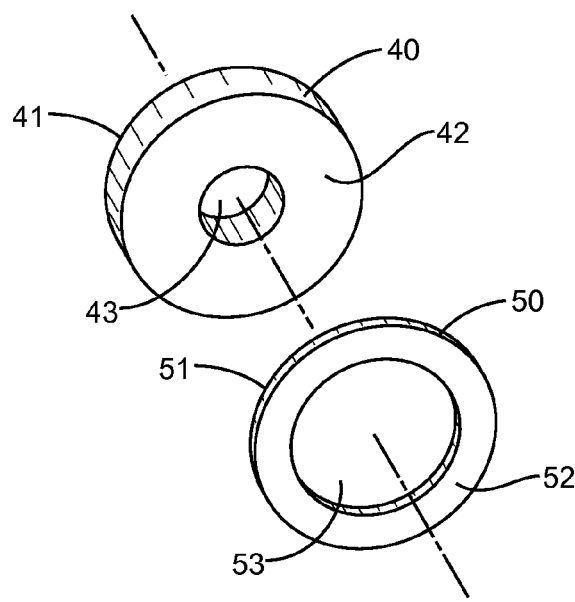
FIG. 10 is an exploded perspective view of a deformable member and a contact member according to one embodiment.
Figure 11:
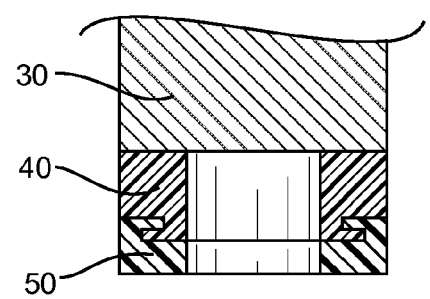
FIG. 11 is a partial schematic sectional view of a set screw with a deformable member according to one embodiment.

The member 40 may also be positioned away from the elongated member 100. FIG. 9 is an embodiment with a contact member 50 positioned on the second side 42 of member 40. The contact member 50 contacts against the member 40 with the member 40 being spaced away from the elongated member 100. Member 40 is deformable and allows for deformation of the contact member 50. In one embodiment as illustrated in FIGS. 9 and 10, contact member 50 is an annular ring with first and second sides 51, 52 and a central aperture 53. The contact member 50 may be aligned with the member 40 such that aperture 53 is centered with the aperture 43. The width of the apertures 43, 53 may vary depending upon the context of use. In one embodiment, a void 94 is formed within the aperture 53. Contact member 50 may be attached to member 40 in various manners, including but not limited to adhesives, molding, and snap fit. FIG. 11 includes an embodiment with the second side 42 of member 40 configured to provide a snap fit with the first side 51 of contact member 50. In one embodiment, the contact member 50 is attached to prevent rotation relative to the member 40.

The contact member 50 may be constructed from various materials, including titanium, stainless steels, cobalt-chrome, and various polymers. The contact member 50 may be constructed from the same or a compatible material with the elongated member 100 to give the set screw a better interface.

FIG. 2 illustrates one embodiment of a fastener 140 that may be used with the set screw 10. In other embodiments as illustrated in FIG. 1, the receiver 150 and anchor 160 include a unitary-one piece construction that does not provide for pivoting movement between the receiver 150 and anchor 160. FIGS. 1 and 2 include top-loading designs that require that the elongated member 100 be loaded into the channel 153 through a top of the receiver 150. Another embodiment includes a side-loading channel 153. One embodiment of a fastener is disclosed in U.S. patent application Ser. No. 11/493,447 herein incorporated by reference.

Figure 12:
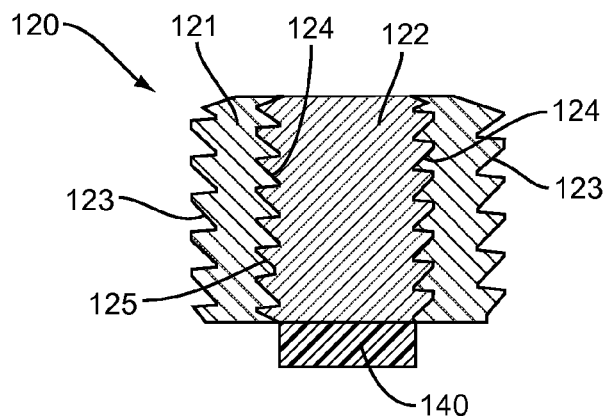
FIG. 12 is a sectional view of a set screw with a deformable member according to one embodiment.

FIG. 12 illustrates a set screw 120 with an outer member 121 and an inner member 122. Outer member 121 includes outer threads 123 for engaging with the receiver 150 as disclosed above. Outer member 121 also includes inner threads 124 to engage with threads 125 on the inner member 122. The outer member 121 may include an annular shape with the inner member 122 sized to fit within the central aperture. The member 140 is positioned at an end of the inner member 122 to contact against the elongated member 100. The ends of the outer member 121 may also contact against the elongated member 100, or may be positioned away from the elongated member 100 when the set screw 120 is attached to the receiver 150.

Figure 13:
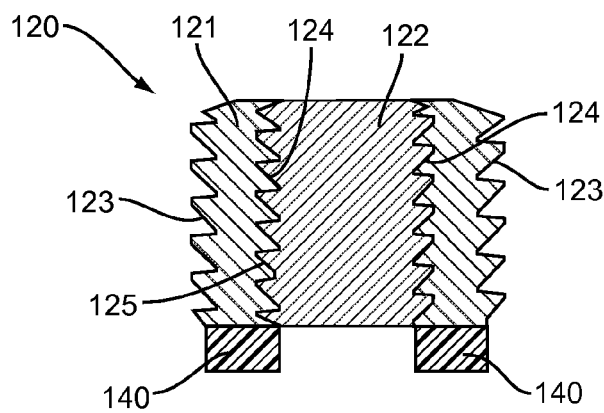
FIG. 13 is a sectional view of a set screw with a deformable member according to one embodiment.

FIG. 13 includes a similar construction with the set screw 120 including inner and outer members 121, 122. The member 140 is attached to the end of the outer member 121. When the set screw 120 is attached to the receiver 150, the member 140 contacts against the elongated member 100. In this embodiment, the member 140 may include an annular shape to extend around the outer member 121 and be spaced from the inner member 122.

Figure 14:
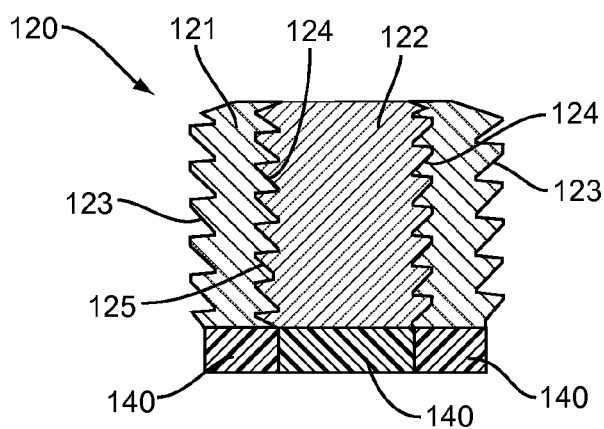
FIG. 14 is a sectional view of a set screw with a deformable member according to one embodiment.

FIG. 14 includes an embodiment of a set screw 120 with both the inner and outer members 121, 122 including members 140. The members 140 may include the same or different construction.

The embodiments of FIGS. 12, 13, and 14 may also include extensions 30 and sidewalls 24 as discussed above to facilitate attachment of the members 140 to the inner and outer members 121, 122.

In use, the fastener 140 is attached to the bone 300 and the elongated member 100 is positioned within the channel 153. The set screw 10 is attached to the receiver 150 and moved into contact with the elongated member 100. The set screw 10 prevents the elongated member 100 from escaping from the channel 153, and also applies a force to secure the elongated member 100 to the receiver 150. The deformable member 40 causes a portion of the set screw 10 to deform around the elongated member 100 to increase an amount of surface area that is in contact with the elongated member. Additionally, the elongated member 100 may not be fully seated within the channel 153 due to the angle the elongated member 100 extends along the bone 300 and the position of the fastener 140. The deformation of the set screw 10 accommodates this positioning and again increases the amount of surface area that the set screw 10 contacts against the elongated member 100. Additionally, this deformation also normalizes the forces applied through the set screw 10 to the elongated member 100 to secure the elongated member 100 in the channel 153.

The elongated member 100 may be constructed from a variety of surgical grade materials. These include metals such as stainless steels, cobalt-chrome, titanium, and shape memory alloys. Non-metallic rods, including polymer rods made from materials such as PEEK and UHMWPE, are also contemplated. The elongated member 100 may be straight, curved, or comprise one or more curved portions along its length.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. In one embodiment, the member 40 includes a greater thickness than contact member 50. In one embodiment, the extension 30 includes a length equal to a thickness of the member 40 and the contact member 50. The present embodiments are, therefore, to be considered in all respects as illustrative and not restrictive, and all changes coming within the meaning and equivalency range of the appended claims are intended to be embraced therein.

What is claimed is:

1. A set screw for use with a receiver to secure an elongated member within a patient, the set screw comprising:
    a body with a first end and second end;
    a sidewall that extends outward from and around a periphery of the second end and forms a recess with the second end;
    an extension that extends outward from the second end, the extension including a base at the second end and a tip at a distal end that faces outward from the body, the extension extending between the base and the tip being straight and coaxial with a centerline of the body;
    an annular member positioned within the recess and extending around the extension, the annular member being attached to the body to prevent rotation of the annular member relative to the body;
    the sidewall, extension and annular member each positioned to space the body away from the elongated member with each positioned to contact against the elongated member when the set screw is engaged with the receiver;
    the annular member constructed from a more deformable material than either the set screw and the receiver to deform against the elongated member.

2. The set screw of claim 1, further comprising a branch that extends outward from the extension at a point between the body and the tip of the extension.

3. The set screw of claim 1, wherein the annular member includes a second end that faces away from the body, the second end being flat.

4. The set screw of claim 1, wherein the body is constructed of a non-PEEK material and the annular member is constructed from PEEK.

5. The set screw of claim 1, wherein the body includes cam surfaces that extend outward from the body between the first and second ends.

* * * * *